United States Patent [19]

Fozzard et al.

[11] 4,182,901

[45] Jan. 8, 1980

[54] DIACYLOXYBUTENE ISOMERIZATION WITH SELENIUM DIOXIDE

[75] Inventors: George B. Fozzard; John R. Norell, both of Bartlesville, Okla.

[73] Assignee: Phillips Petroleum Company, Bartlesville, Okla.

[21] Appl. No.: 841,780

[22] Filed: Oct. 13, 1977

[51] Int. Cl.$^2$ .............................................. C07C 67/28
[52] U.S. Cl. .................... 560/262; 252/430; 560/100; 560/112; 560/248
[58] Field of Search ............... 560/262, 100, 106, 112

[56] References Cited

U.S. PATENT DOCUMENTS

| | | | |
|---|---|---|---|
| 2,575,896 | 11/1951 | Smith et al. | 560/262 |
| 3,715,389 | 2/1973 | Hoch et al. | 260/497 R |
| 3,755,423 | 8/1973 | Onoda et al. | 260/497 A |
| 3,778,468 | 12/1973 | Kollar | 260/497 R |
| 3,830,833 | 8/1974 | Shunsuke et al. | 560/262 |
| 3,872,163 | 3/1975 | Shimizu et al. | 560/262 |
| 4,095,030 | 6/1978 | Stapp | 560/262 |
| 4,121,039 | 10/1978 | Parthasarathy et al. | 560/112 |

FOREIGN PATENT DOCUMENTS 1170222  11/1969  United Kingdom.

OTHER PUBLICATIONS

Chem. Abstracts, 76, 72040e.
Chem. Abstracts, 78, 71480c.
Chem. Abstracts, 83, 96447p.

*Primary Examiner*—Vivian Garner

[57] ABSTRACT

Diacyloxyolefins are isomerized by contacting one or more diacyloxyolefins with a catalyst system comprising selenium dioxide and a suitable carboxylic acid. There can be additionally present in the catalyst system at least one compound selected from the group consisting of a carboxylic acid anhydride, a polar compound, and an ionic reagent.

28 Claims, No Drawings

DIACYLOXYBUTENE ISOMERIZATION WITH SELENIUM DIOXIDE

BACKGROUND OF THE INVENTION

This invention relates to the isomerization of diacyloxyolefins.

A number of chemicals can be made from diacyloxyolefins. More specifically, a diacyloxyolefin can easily be converted to various valuable chemicals such as diols, furans, and polyesters. For example, by means of various processes known in the art, 1,3-butadiene can be converted to a mixture of 1,4-diacyloxy-2-butene and its isomer 1,2-diacyloxy-3-butene. Since the 1,2,-isomer is the more volatile of the two, the 1,4-isomer can be separated from the 1,2-isomer by fractional distillation. The 1,4-isomer can then be hydrogenated to remove the double bond and to produce 1,4-diacyloxybutane which can be converted to tetrahydrofuran by hydrolysis and cyclization. This overall process to convert 1,3-butadiene to tetrahydrofuran could be substantially simplified by including an isomerization step to convert the 1,2-isomer to the 1,4-isomer.

An object of this invention is to provide a process for isomerization of diacyloxyolefins.

Another object of this invention is to provide a catalyst system for isomerization of a diacyloxyolefin to the desired isomer.

The instant invention is suitable for the isomerization of diacyloxyolefins represented by the general formulas I and II shown below:

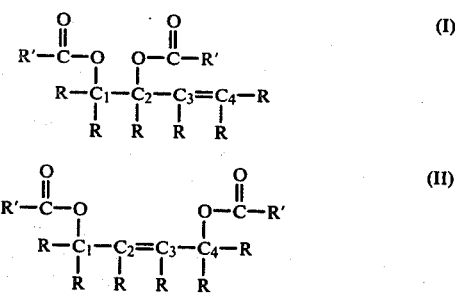

wherein each R is individually selected from the group consisting of hydrogen or an alkyl radical of from 1-4 carbon atoms, and wherein R' can be R or any aryl radical of from 6-10 carbon atoms, and wherein at least one of the R's attached to the carbon atoms numbered 1 and 4 carbon atoms numbered 1 and 4 in formulas I and II is hydrogen.

Further objects, advantages, details and embodiments of this invention will become apparent to those skilled in the art from the following detailed description of the invention, the examples, and the appended claims.

In accordance with the present invention there is provided a process for the isomerization of diacyloxyolefins which comprises contacting under isomerization conditions at least one diacyloxyolefin with a catalyst system formed by admixing selenium dioxide and a carboxylic acid represented by the general formula

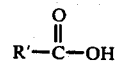

wherein R' is selected from the group consisting of hydrogen, an alkyl radical of from 1-4 carbon atoms, and an aryl radical of from 6-10 carbon atoms. Additionally present in the catalyst system can be at least one compound selected from the group consisting of a carboxylic acid anhydride, a polar compound, and an ionic reagent.

The instant invention also provides an isomerization system for converting diacyloxyolefins of general formula I to isoméric compounds of general formula II or for converting diacyloxyolefins of general formula II to isomeric compounds of general formula I. For example, 1,2-diacetoxy-3-butene can be isomerized to a mixture of 1,2-diacetoxy-3-butene and 1,4-diacetoxy-2-butene from which 1,4-diacetoxy-2-butene can be separated and 1,2-diacetoxy-3-butene recycled to the isomerization step. Likewise, 1,4-diacetoxy-2-butene can be isomerized to a mixture of 1,2-diacetoxy-3-butene and 1,4diacetoxy-2-butene from which 1,2-diacetoxy-3-butene can be separated and 1,4-diacetoxy-2-butene recycled to the isomerization step. It is recognized that the maximum extent of isomerization achieved according to the instant invention will be limited according to the equilibrium composition for the system assuming that no steps are taken to upset the equilibrium. The position of the equilibrium can generally be determined by following the extent of isomerization with time when starting with a single isomeric compound or preferably utilizing separately both isomers in two such runs. For economic reaons, the equilibrium isomer composition need not be reached and the isomerization reaction can be terminated after a convenient time and the reaction product separated.

Compounds represented by general formula I and II above are conveniently prepared by the oxidation of conjugated butadiene in the presence of a carboxylic acid represented by the general formula R'—CO$_2$H wherein R' is selected from the group consisting of hydrogen, an alkyl radical of from 1-4 carbon atoms, or an aryl radical of from 6-10 carbon atoms.

The diacyloxyolefins suitable for use in the invention can be selected from a large variety of compounds. Some examples of compounds represented by genrla formula I which can be employed in the instant invention include 1,2-diacetoxy-3-butene, 1,2-diacetoxy-3-methyl-3-butene, 1,2-diformyloxy-3-butene, 1,2-dibenzoxy-3-butene, 1,2-d-1-naphtholyloxy-3-butene, 1,2-dipropionyloxy-3-butene, 1,2-diacetoxy-2,3-dimethyl-3-butene. Some examples of compounds represented by general formula II which can be employed in the instant invention include 1,4-diacetoxy-2-butene, 1,4-diacetoxy-2-methyl-2-butene, 1,4-diformyloxy-2-butene, 1,4-dibenzoxy-2-butene, 1,4-naphthoyloxy-2-butene, 1,4-di-propionyloxy-2-butene, 1,4-diacetoxy-2,3-dimethyl-2-butene.

The diacyloxybutenes are a preferred group of reactants with the diacetoxybutenes being especially preferred because of availability, reactivity, and important utility.

Suitable mixtures, i.e., non-equilibrium mixtures, of isomeric compounds corresponding to formulas I and II can, of course, also be employed in the process of this invention. For example, the instant invention can be employed to treat non-equilibrium mixtures of isomers of types I and II noted above to enrich the mixture in one or the other isomer depending on the starting composition of the mixture. From a practical standpoint, it is envisioned that the instant invention will be of greater benefit in the treatment of non-equilibrium mixtures.

The isomerization of the diacyloxyolefin described above is preferably achieved by contacting under isomerization conditions a diacyloxyolefin with a catalyst system formed by admixing selenium dioxide and a carboxlyic acid represented by the general formula

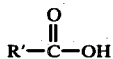

wherein R' is selected from the group consisting of hydrogen, an alkyl radical of from 1-4 carbon atoms, or an aryl radical of from 6-10 carbon atoms.

It is preferred for the practice of the isomerization of the instant invention that the R' in the carboxylic acid and in the diacyloxyolefin be the same.

Some examples of suitable carboxylic acids are acetic acid, formic acid, benzoic acid, 1-naphthoic acid, and propionic acid.

The most preferred carboxylic acid utilized in this invention is acetic acid.

The amount of carboxylic acid employed for the process of this invention is generally within the range of 0.005–100 liters per mole of diacyloxyolefin and preferably within the range of 0.1–10 liters pr mole of diacyloxyolefin.

The amount of selenium dioxide employed for the process of this invention is generally within the range of 0.0001–0.4 moles per mole of diacyloxyolefin or mixture thereof and preferably within the range of 0.001–0.2 moles per mole of diacyloxyolefin. Higher levels of selenium dioxide may be used, but will not appreciably aid the isomerization.

In another embodiment of this invention, the isomerization system can also additionally have at least one compound selected from the group consisting of a carboxylic acid anhydride, a polar compound, and an ionic reagent present therein.

The suitable carboxlyic acid anhydride is represented by the general formula

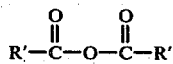

wherein R' is selected from the group consisting of hydrogen, alkyl radicals of from 1-4 carbon atoms, or an aryl radical of from 6-10 carbon atoms.

The R' in the carboxylic acid anhydride should be the same as that in the starting diacyloxyolefin.

Some examples of suitable carboxylic acid anhydrides for the isomerization of the instant invention include acetic anhydride, benzoic anhydride, 1-naphthoic anhydride, propionic anhydride.

The preferred carboxylic acid anhydride utilized in this invention is acetic anhydride.

The amount of carboxylic acid anhydride employed for the process of this invention is generally within the range of 0.005–100 liters per mole of diacyloxyolefin and preferably within the range of 0.1–10 liters per mole of diacyloxyolefin.

The polar compounds should have a dielectric constant of at least 10 when measured within the temperature range of 20°–30° C. and should be essentially inert under the isomerization conditions.

Some examples of suitable polar compounds are those selected from the group consisting of pyridine, 1-methyl-2-pyrrolidinone, N,N-dimethylformamide, N,N-dimethylacetamide, hexamethylphosphoramide, benzonitrile, acetonitrile, dimethyl sulfoxide, sulfolane.

The amount of polar compound employed for the process of this invention is generally within the range of 0.005–100 liters per mole of diacyloxyolefin and preferably within the range of 0.1–10 liters per mole of diacyloxyolefin.

The ionic reagent utilized is selected from the group consisting of the alkali metal, alkaline earth metal, and ammonium hydroxides or salts of a carboxylic acid represented by the general formula

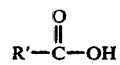

wherein R' is selected from the group consisting of hydrogen, an alkyl radical of from 1-4 carbon atoms, or an aryl radical of from 6-10 carbon atoms.

As used herein, the term "alkali metal" denotes the metals lithium, sodium, potassium, rubidium, and cesium while the term "alkaline earth metal" denotes the metals beryllium, magnesium, calcium, strontium, and barium. Some examples of suitable ionic reagents include sodium acetate, lithium formate, potassium benzoate, cesium propionate, ammonium acetate, sodium butyrate, potassium 1-naphthoate, beryllium acetate, magnesium formate, calcium benzoate, strontium acetate, barium acetate, ammonium benzoate, lithium hydroxide, sodium hydroxide, potassium hydroxide, cesium hydroxide, ammonium hydroxide, beryllium hydroxide, magnesium hydroxide, calcium hydroxide, strontium hydroxide, barium hydroxide.

The amount of ionic reagent employed for the process of this invention is not critical and can be selected from a relatively broad range of amounts. Generally the amount is within the range of 0.001–5 moles per mole of starting diacyloxyolefin or mixture thereof with a preferable range of 0.05–2 moles per mole of diacyloxyolefin.

The R' in the carboxylate salt should be the same as that in the starting diacyloxyolefin. For example, an acetate salt should be used when a diacetoxyolefin is to be isomerized.

The isomerization reaction of this invention is carried out at a temperature that can be selected over a broad range. Generally, the temperature ranges from about 150° C. to about 360° C. preferably from about 175° C. to about 250° C.

The time utilized for the isomerization reaction will depend on temperature, the component concentration, and on the extent of isomerization desired. In some instances, the reaction may be conducted for a few minutes or for as long as 24 hours and longer. Thus, in most instances, reaction time is not considered to be a significant parameter of the invention.

The isomerization reaction according to this invention is preferably carried out at a pressure sufficient to maintain the system in the liquid phase which often is autogenous pressure. However, the reaction can be conducted in the presence of an added inert gas such as nitrogen at atmospheric or super-atomspheric pressure. The latter condition may be employed in those instances wherein a relatively low boiling material is used at a relatively high temperature in order to maintain a predominantly liquid phase system.

In a presently preferred embodiment of this invention the isomerization reaction mixture is homogenous as compared to a heterogenous mixture. In any event, conventional liquid phase mixing procedures can be utilized during the reaction period in this invention.

The presence of water in the reaction mixture can give rise to the production of hydroxyolefin compounds which may be very difficult to separate from the diaclyoxyolefins. For this reason, it is preferred to operate under essentially anhydrous conditions.

The isomerization reaction product obtained according to the instant invention can be filtered to remove any solid material and subjected to fractional distillation to separate the desired diacyloxyolefin. The other diacyloxyolefin can then be recycled.

When using a polar compound that has appreciable water solubility, it may be desirable to extract the reaction mixture with water and thereafter separate the diacyloxyolefin mixture by fractional distillation. Said water extraction should be conducted under conditions which do not promote hydrolysis of diacyloxyolefins, e.g., at temperatures below about 70° C. Furthermore, traces of water should be removed from the residual diacyloxyolefins before distillation in order to avoid hydrolysis. Other suitable separation methods can be employed in the separation of the reaction mixture components.

Generally, this invention will find broadest utility in the isomerization of type I compounds to type II compounds. Type II compounds can be hydrogenerated and cyclized to tetrahydrofurans or pyrrolidones. Alternatively, they can be hydrogenated then hydrolyzed to 1,4-diols which are useful as solvents or monomers in the preparation of polyesters of polyurethanes. Especially important in this regard is 1,4-butanediol which is employed in the production of polybutylene terephthalate, an important polyester resin which highly desirable properties.

However, this invention can also be utilized to isomerize type II compounds to type I compounds. The type I compounds can be hydrogenated and hydrolyzed to yield vicinal diols that are useful as sensitizers and fog inhibitors for photographic emulsions, for the production of polyurethane coatings having improved viscosity stability, and for the production of polyester films with improved stability for use in electrical condensers.

The following Examples will further illustrate the invention.

EXAMPLE I

A series of runs were conducted according to the instant invention using cis-1,4-diacetoxy-2-butene.

In each run the reaction was carried out in a 120 ml Fischer-Porter aerosol compatibility bottle equipped with a magnetic stirrer, thermocouple, and heating mantle. The bottle was charged with 150 ml acetic acid, 10 ml acetic anhydride, 1.0 g (42 mmoles) lithium hydroxide, 1.1 g (10 mmole) selenium dioxide, and 8,7 g (51 mmoles) cis-1,4-diacetoxy-2-butene. Also added to the above was 2.0 g 1,3-diacetoxypropane—an internal standard for gas-liquid chromatographic (glc) analysis. This glc standard was not a necessary component to effect isomerization.

Each reaction mixture was heated to about 200° C. and samples were taken at several points during the reaction for later analysis. The samples taken during the reaction and the final reaction mixture were analyzed directly by gas-liquid chromatography (glc) and the results are shown in Table I.

TABLE I

| Run No. | Temp., °C. | Press.,(a) psig (MPa) | Time,(b) min. | 1,2-diacetoxy-3-butene, % | cis-1,4-diacetoxy-2-butene, % | trans-1,4-diacetoxy-2-butene, % |
|---|---|---|---|---|---|---|
| 1 | 185 | 90(0.62) | 15 | 7.6 | 92.4 | — |
|   | 200 | 84(0.58) | 131 | 9.3 | 90.7 | — |
|   | 200 | 86(0.59) | 247 | 10.2 | 81.9 | 7.9 |
|   | (c) |  |  | 12.4 | 79.9 | 7.8 |
| 2 | 200 | 82(0.56) | 64 | 18 | 75 | 7 |
|   | 195 | 80(0.55) | 194 | 18 | 72 | 11 |
|   | 195 | 85(0.59) | 324 | 21 | 64 | 15 |
|   | (d) |  |  | 22 | 59 | 20 |

(a)MPa = mega Pascale
(b)Amount of time after the reaction mixture reached a temperature of about 200° C.
(c)Reaction mixture at the end of the reaction.
(d)Reaction mixture after standing overnight at room temperature.

The results of Table I demonostrate that the system of the instant invention isomerized cis-1,4-diacetoxy-2-butene to 1,2-diacetoxy-3-butene. Under the reaction conditions there was alos some isomerization of cis-1,4-diacetoxy-2-butene to trans-1,4-diacetoxy-2-butene.

The isomerization of diacyloxyolefins is an equilibrium process and an equilibrium mixture can be approached from either isomer. Since the isomerization of cis-1,4-diacetoxy-2-butene to 1,2-diacetoxy-3-butene under the conditions of this invention has been established, the isomerization of 1,2-diacetoxy-3-butene to 1,4-diacetoxy-2-butene is expected to occur under these isomerization conditions.

EXAMPLE II

A further run was carried out in essentially the same manner as in Runs 1 and 2 of Example I except that selenium dioxide was not included. The same type of vessel as in Example I was charged with 80 ml acetic acid, 5 ml acetic anhydride, 2.0 g. (84 mmoles) lithium hydroxide, 16.2 g. (94 mmole) cis-1,4-diacetoxy-2-butene, and 2.0 g. 1,3-diacetoxypropane (an internal glc standard). The reation mixture was heated (about 200° C.) with stirring for 393 minutes.

Analysis (glc) of samples taken during the run and of the final reaction mixture showed no detectable amounts of 1,2-diacetoxy-3-butene. There was no significant amount of cis-1,4-diacetoxy-2-butene to trans-1,4-diacetoxy-2-butene isomerization under the reaction conditions.

The results of this control run show that essentially no isomerization of cis-1,4-diacetoxy-2-butene to 1,2-diacetoxy-3-butene occurs in the absence of selenium dioxide.

Reasonable variations and modifications, which will become apparent to those skilled in the art, can be made in this invention without departing from the spirit and scope thereof.

We claim:

1. A process for the isomerization of diacyloxyolefins which comprises contacting at least one diacyloxyolefin of the formula

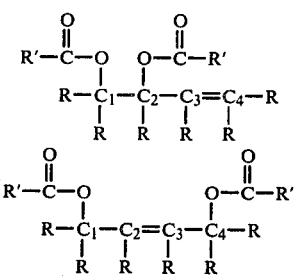

wherein each R is individually selected from the group consisting of hydrogen or an alkyl radical of from 1 to 4 carbon atoms, and wherein R' can be R or an aryl radical of from 6 to 10 carbon atoms, and wherein at least one of the R's attached to the carbon atoms numbered 1 and 4 in said formulas I and II is hydrogen with a catalyst system formed by admixing selenium dioxide and a carboxlyic acid represented by the general formula

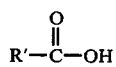

wherein R' is selected from the group consisting of hydrogen, an alkyl radical of from 1-4 carbon atoms, and an aryl radical of from 6-10 carbon atoms at a pressure sufficient to maintain the system in the liquid phase.

2. A process for the isomerization of diacyloxyolefins which comprises contacting at least one diacyloxyolefin of the formula

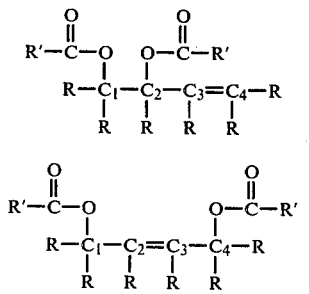

wherein each R is individually selected from the group consisting of hydrogen or an alkyl radical of from 1 to 4 carbon atoms, and wherein R' can be R or an aryl radical of from 6 to 10 carbon atoms, and wherein at least one of the R groups attached to the carbon atoms numbered 1 and 4 in said formulas I and II is hydrogen with a catalyst system formed by admixing selenium dioxide and a carboxylic acid represented by the general formula

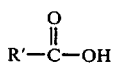

wherein R' is selected from the group consisting of hydrogen, an alkyl radical of from 1-4 carbon atoms, and an aryl radical of from 6-10 carbon atoms wherein said process is carried out at a temperature in the range of from about 150° C. to about 360° C. and at a pressure sufficient to maintain the system in the liquid phase.

3. The process of claim 2 wherein the R' in the carboxylic acid and diacyloxyolefin is the same.

4. The process of claim 2 wherein the said diacyloxyolefin of formula I is selected from the group consisting of 1,2-diacetoxy-3-butene, 1,2-diacetoxy-3-methyl-3-butene, 1,2-diformyloxy-3-butene, 1,2-dibenzoxy-3-butene, 1,2-di-1-naphthoyloxy-3-butene, 1,2-dipropionyloxy-3-butene and 1,2-diacetoxy-2,3-dimethyl-3-butene.

5. The process of claim 2 wherein the said diacyloxyolefin of formula II is selected from the group consisting of 1,4-diacetoxy-2-butene, 1,4-diacetoxy-2-methyl-2-butene, 1,4-diformyloxy-2-butene, 1,4-dibenzoxy-2-butene, 1,4-di-1-naphthoyloxy-2-butene, 1,4-dipropionyloxy-2-butene and 1,4-diacetoxy-2,3-dimethyl-2-butene.

6. The process of claim 2 wherein the said diacyloxyolefin is cis-1,4-diacetoxy-2-butene.

7. The process of claim 2 wherein the said carboxylic acid is selected from the group consisting of acetic acid, formic acid, benzoic acid, 1-naphthoic acid and propionic acid.

8. The process of claim 2 wherein the said carboxylic acid is acetic acid.

9. The process of claim 2 wherein the temperature is in the range from about 175° C. to about 250° C. and the pressure is sufficient to maintain the system in the liquid phase.

10. The process of claim 2 wherein said selenium dioxide is employed in the range of from about 0.0001 to about 0.4 moles per mole of diacyloxyolefin and said carboxylic acid is present in an amount in the range of from about 0.005 to about 100 liters per mole of diacyloxyolefin.

11. The process of claim 2 wherein the amount of selenium dioxide employed is in the range of from about 0.01 to about 0.2 moles per mole of diacyloxyolefin and the amount of carboxylic acid employed is in the range of from about 0.1 to about 10 liters per mole of diacyloxyolefin.

12. The process of claim 2 wherein the desired isomerized diacyloxyolefin is recovered as a product of the process.

13. The process of claim 12 wherein the desired isomerized diacyloxyolefin is recovered by fractional distillation.

14. The process of claim 12, wherein the diacyloxyolefin that is not recovered is recycled to the reaction mixture.

15. A process for the isomerization of diacyloxyolefins which comprises contacting at least one diacyloxyolefin of the formula

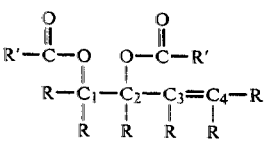

-continued

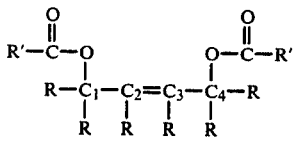
(II)

wherein each R is individually selected from the group consisting of hydrogen or an alkyl radical of from 1 to 4 carbon atoms, and wherein R' can be R or an aryl radical of from 6 to 10 carbon atoms, and wherein at least one of the R groups attached to the carbon atoms numbered 1 and 4 in said formulas I and II is hydrogen with a catalyst system formed by admixing selenium dioxide, a carboxylic acid represented by the general formula

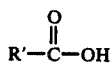

wherein R' is selected from the group consisting of hydrogen, an alkyl radical of from 1–4 carbon atoms, and an aryl radical of from 6–10 carbon atoms and at least one compound selected from the group consisting of a carboxylic acid anhydride, a polar compound, and an ionic reagent wherein the said polar compound has a dielectric constant of at least 10 when measured within a temperature range of 20°–30° C. and wherein said ionic reagent is selected from the group consisting of the alkali metal, alkaline earth metal, and ammonium hydroxides or salts of a carboxylic or salts of a carboxylic acid represented by the general formula

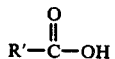

wherein R' is selected from the group consisting of hydrogen, an alkyl radical of from 1–4 carbon atoms, or an aryl radical of from 6–10 carbon atoms wherein said process is carried out at a temperature in the range of from about 150° to about 360° C. and at a pressure sufficient to maintain the system 20 in the liquid phase.

16. The process of claim 15 wherein the said polar compound is selected from the group consisting of pyridine, 1-methyl-2-pyrrolidinone, N,N-dimethylformamide, benzonitrile, acetonitrile, dimethyl sulfoxide, and sulfolane.

17. The process of claim 15 wherein the amount of said polar compound employed ranges from about 0.005 to about 100 liters per mole of diacyloxyolefin.

18. The process of claim 15 wherein the amount of said polar compound employed ranges from about 0.1 to about 10 liters per mole of diacyloxolefin.

19. The process of claim 15 wherein the amount of said ionic reagent employed ranges from about 0.001 to about 5 moles per mole of diacyloxyolefin.

20. The process of claim 15 wherein the amount of said ionic reagent employed ranges from about 0.05 to about 2 moles per mole of diacyloxyolefin.

21. The process of claim 12 wherein the said ionic reagent is selected from the group consisting of sodium acetate, lithium formate, potassium benzoate, cesium propionate, ammonium acetate, sodium butyrate, potassium 1-naphthoate, beryllium acetate, magnesium formate, calcium benzoate, strontium acetate, barium acetate, ammonium benzoate, lithium hydroxide, sodium hydroxide, potassium hydroxide, cesium hydroxide, ammonium hydroxide, beryllium hydroxide, magnesium hydroxide, calcium hydroxide, strontium hydroxide and barium hydroxide.

22. The process of claim 21 wherein the said ionic reagent is lithium hydroxide.

23. The process of claim 13 wherein the said carboxylic acid anhydride is represented by the general formula

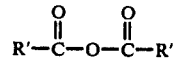

wherein R' is selected from the group consisting of hydrogen, alkyl radicals of from 1–4 carbon atoms, or aryl radicals of from 6–10 carbon atoms.

24. The process of claim 23 wherein the R' in the carboxylic acid anhydride and diacyloxyolefin is the same.

25. The process of claim 23 wherein the said carboxylic acid anhydride is selected from the group consisting of acetic anhydride, benzoic anhydride, 1-naphthoic anhydride, propionic anhydride.

26. The process of claim 25 wherein the said carboxylic acid anhydride is acetic anhydride.

27. The process of claim 23 wherein the amount of said carboxylic acid anhydride employed ranges from about 0.005 to about 100 liters per mole of diacyloxyolefin.

28. The process of claim 23 wherein the amount of said carboxylic acid anhydride employed ranges from about 0.1 to about 10 liters per mole of diacyloxyolefin.

* * * * *

UNITED STATES PATENT AND TRADEMARK OFFICE
CERTIFICATE OF CORRECTION

PATENT NO. : 4,182,901

DATED : January 8, 1980

INVENTOR(S) : George B. Fozzard et al

It is certified that error appears in the above—identified patent and that said Letters Patent are hereby corrected as shown below:

Column 8, line 45, claim 11, "0.01" should be --- 0.001 ---.

Column 8, line 56, claim 14, after "claim 12", delete ",".

Column 9, line 34, claim 15, after "carboxylic", delete "or salts of a carbox-"

line 35, delete "ylic".

Column 9, line 47, claim 15, after "system" delete "20".

Column 10, line 13, claim 21, after "claim" delete "12" and insert --- 15 ---.

Column 10, line 26, claim 23, after "claim" delete "13" and insert --- 15 ---.

Column 10, line 43, claim 25, after "anhydride", delete "," and insert --- and ---.

Signed and Sealed this

Twenty-third Day of December 1980

[SEAL]

Attest:

SIDNEY A. DIAMOND

Attesting Officer

Commissioner of Patents and Trademarks